United States Patent
Xu

(10) Patent No.: US 10,005,778 B2
(45) Date of Patent: Jun. 26, 2018

(54) METHOD FOR PREPARING PALBOCICLIB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days. days.

(21) Appl. No.: 15/596,574

(22) Filed: May 16, 2017

(65) Prior Publication Data

US 2017/0247380 A1 Aug. 31, 2017

Related U.S. Application Data

(63) Continuation of application No. PCT/CN2015/089738, filed on Sep. 16, 2015.

(30) Foreign Application Priority Data

Nov. 26, 2014 (CN) .......................... 2014 1 0693091

(51) Int. Cl.
*C07D 471/04* (2006.01)
(52) U.S. Cl.
CPC ................... *C07D 471/04* (2013.01)
(58) Field of Classification Search
CPC .................................................. C07D 471/04
See application file for complete search history.

(56) References Cited

U.S. PATENT DOCUMENTS

2004/0236084 A1 11/2004 Biwersi et al.

FOREIGN PATENT DOCUMENTS

| CN | 101001857 A | 7/2007 |
|----|-------------|--------|
| CN | 101511829 A | 8/2009 |
| CN | 103501789 A | 1/2014 |
| CN | 104496983 A | 4/2015 |
| WO | 2003062236 A1 | 7/2003 |
| WO | 2008032157 A2 | 3/2008 |
| WO | 2012018540 A1 | 2/2012 |
| WO | 2012068381 A2 | 5/2012 |

*Primary Examiner* — Bruck Kifle
(74) *Attorney, Agent, or Firm* — Perkins Coie LLP

(57) ABSTRACT

This invention reveals the method for preparing Palbociclib (I). The preparation includes: produce the 6-acetyl-5-methyl-2-substituent-pyrido[2,3-d]pyrimidin-7(8H)-one (IV) through the ring-closure reaction by using accessible raw materials of 1-(4-amino-2-substituent-5-pyrimidinyl) ethanone (II) and acetylacetic ester (III); produce the 6-acetyl-8-cyclopentyl-5-methyl-2-substituent-pyrido[2,3-d]pyrimidin-7(8H)-one (VI) through the substitution reaction between the intermediate (IV) and the cyclopentane halide (V); prepare the Palbociclib (I) through the condensation and hydrolysis reactions between the intermediate (VI) and 4-(6-amino-3-pyridinyl)-1-piperazinecarboxylic acid 1,1-dimethylethyl ester (VII). This method for preparing Palbociclib (I) is characterized by easily available raw materials, concise process and economy and environmental protection, and it is suitable for industrialized production.

9 Claims, No Drawings

METHOD FOR PREPARING PALBOCICLIB

CROSS REFERENCE TO RELATED APPLICATIONS

This application is a continuation of PCT/CN2015/089738 filed 2015 Sep. 16, which claims priority to CN 201410693091.1 filed 2014 Nov. 26, both of which are incorporated herein by reference.

TECHNICAL FIELDS

This invention belongs to the technical fields of organic synthesis route design and preparation of APIs and intermediates, and it especially involves the method for preparing the drug Palbociclib which may be used for the treatment of breast cancer.

BACKGROUND ART

Palbociclib is a cyclin-dependent kinase (CDK4/6) inhibitor developed by Pfizer Inc. It obtained the qualification of "breakthrough therapy" from the U.S. FDA in April 2013. Because of its good clinical performance in Phase III, in August 2014, Pfizer Inc. submitted an application for going on sale to the U.S. FDA and obtained the prioritized examination qualification, and used it for first-line treatment of advanced breast cancer of estrogen receptor positive (ER+) and human epidermal growth factor receptor 2 negative (HER2−). Successful research of this drug will provide another important choice for the patients with metastatic breast cancer. This drug does not have a standard Chinese translation yet, so the applicant hereby transliterates it as "帕博西尼".

Chemical name of Palbociclib (I) is: 6-acetyl-8-cyclopentyl-5-methyl-2-[[5 -(1-piperazinyl)-2-pyridinyl]amino]-pyrido[2,3-d]pyrimidin-7(8H)-one, and its structural formula is:

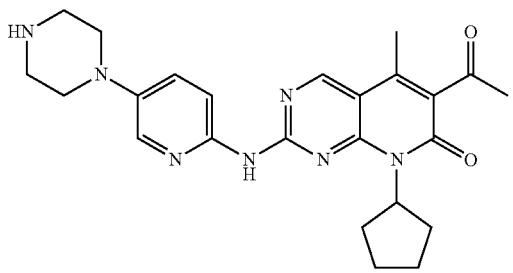 [SMILES: CC(=O)c1c(C)c2cnc(Nc3ccc(N4CCNCC4)cn3)nc2n(C2CCCC2)c1=O]

Palbociclib (I)

The synthesis method of Palbociclib was reported in the brand-name drug company's PCT patents such as WO2003062236, WO2008032157, WO2012018540 and WO2012068381 as well as the literature on Pages 2388-2406 in 2005 Vol. 48 in *J. Med. Chem*. Its preparation mainly includes two synthesis routes.

Route 1:

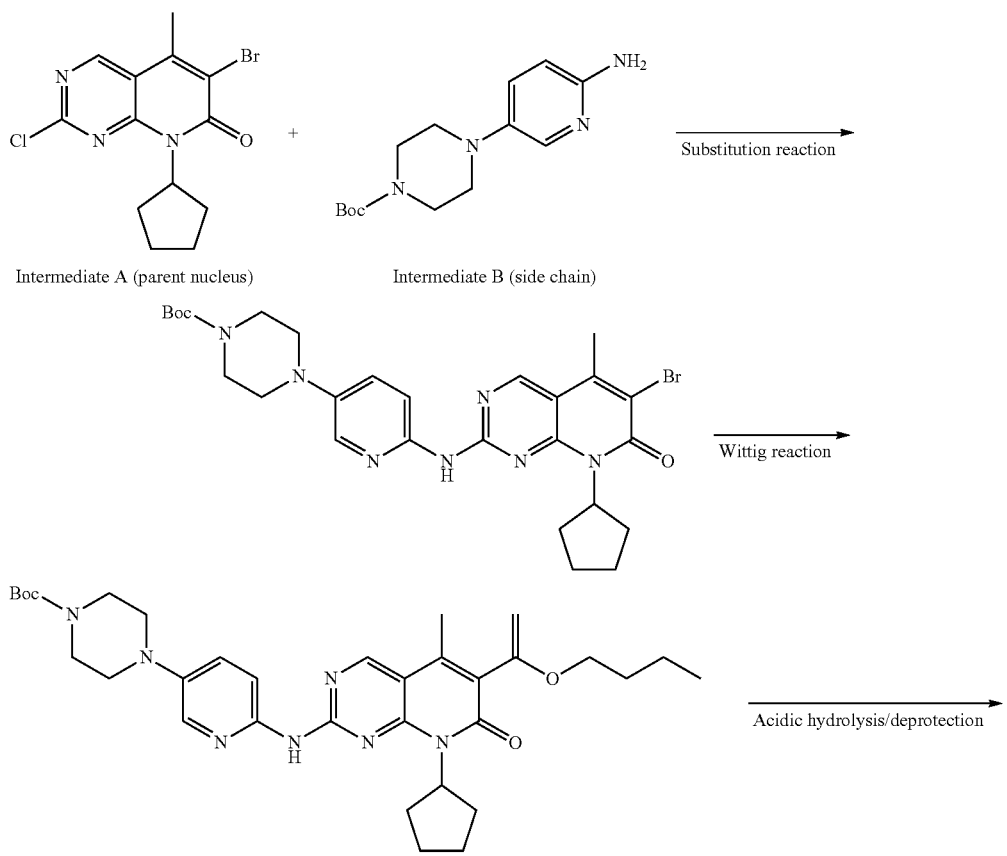

-continued
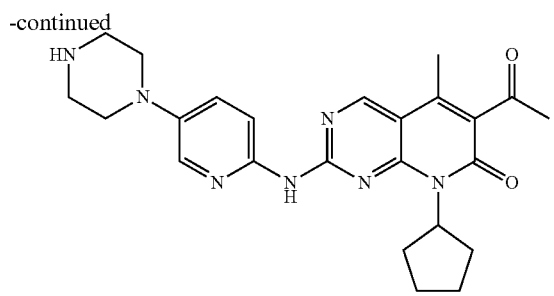
Palbociclib (I)
In Route 1, intermediate A (parent nucleus) and intermediate B (side chain) are taken as the raw materials, and Palbociclib (I) is prepared through the reactions such as substitution reaction, Wittig olefination, acid hydrolysis (rearrangement) and de-protection.
Route 2:
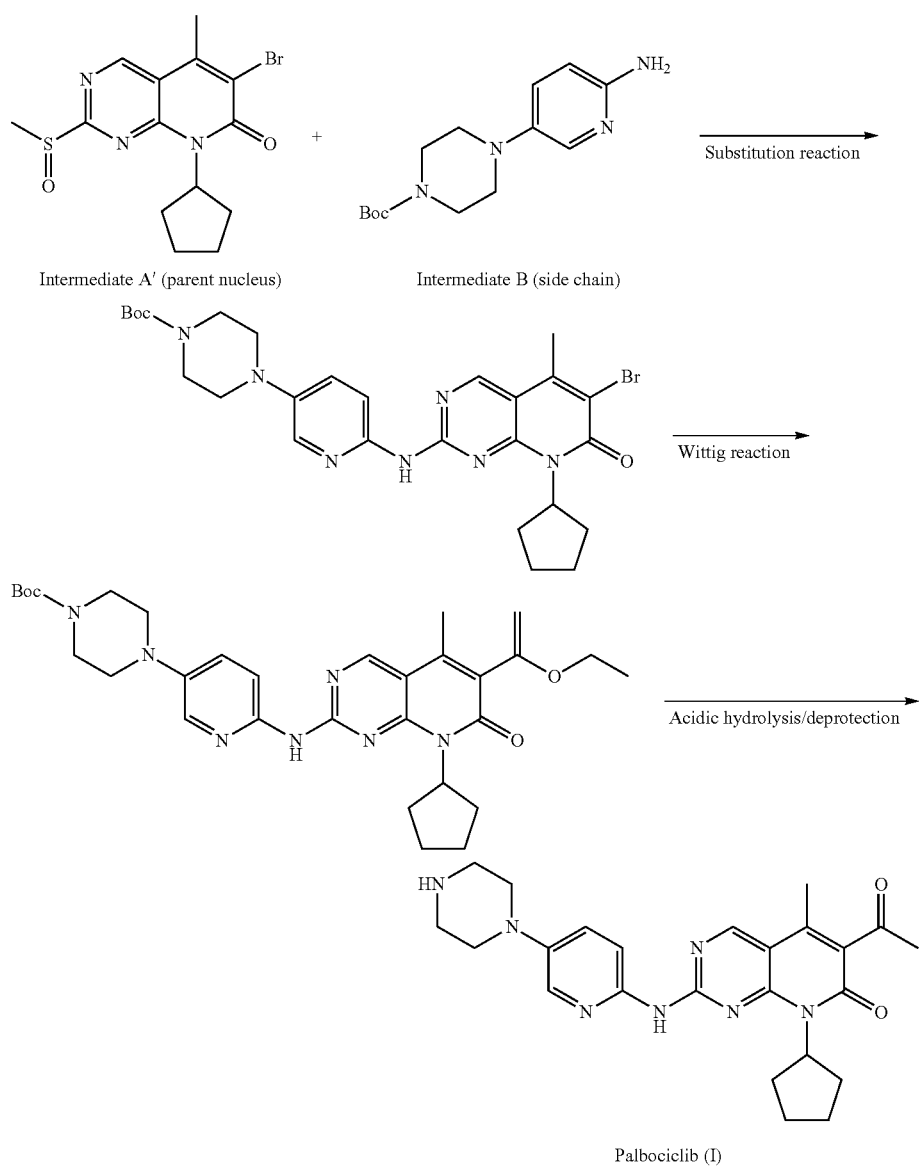
Palbociclib (I)

In Route 2, Palbociclib (I) is prepared through the reactions of the changed intermediate A' (parent nucleus) and intermediate B (side chain) and then through 6-position modification and de-protection.

Through analysis of the above two synthesis routes, the main difference between them is the difference in 2-position substituent groups of intermediates A and A' (parent nucleus). The intermediate A in Route 1 is 2-halogen (chlorine), and the intermediate A' in Route 2 is 2-methylsulfinyl group; obviously, the selective difference between 2-methylsulfinyl group and 6-halogen (bromine) in the intermediate A' is greater than the selective difference between two halogens (chlorine and bromine) in the intermediate A, so the synthesis design in Route 2 avoids a competitive side reaction caused due to two halogens with similar reactivity in Route 1, and greatly improves reaction yield and product purity. However, synthesis of the core intermediates A and A' (parent nucleus) is relatively complex no matter for Route 1 or Route 2. Its main raw materials 2,5,6-trisubstituted pyrimidine rings are hard to come by, and there are disadvantages such as various reaction steps and complex side reactions, which greatly limits industrial production of this drug.

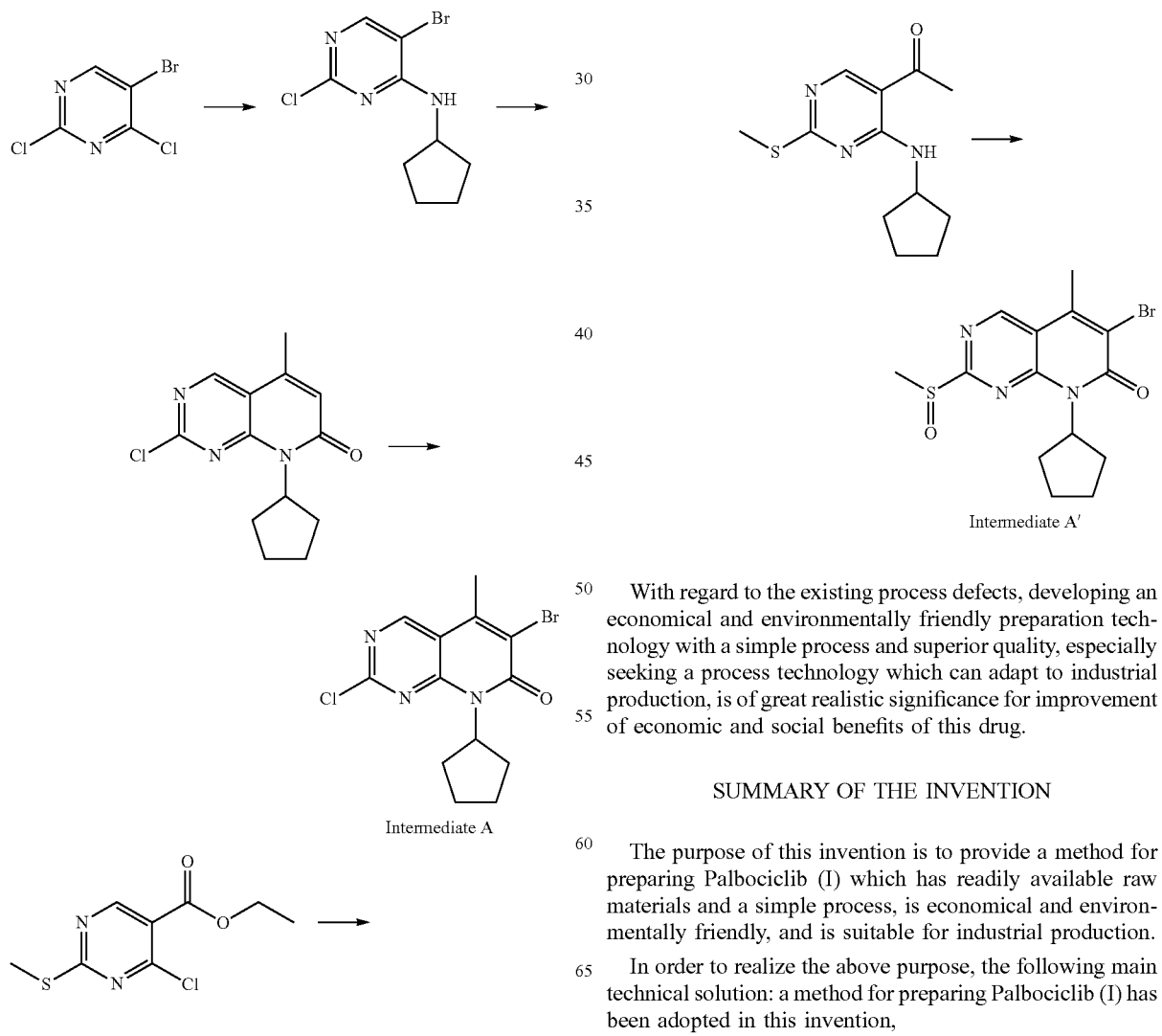

Intermediate A

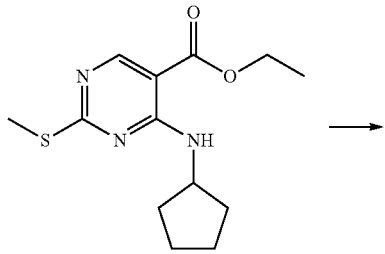

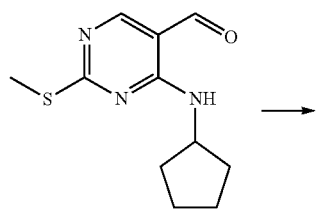

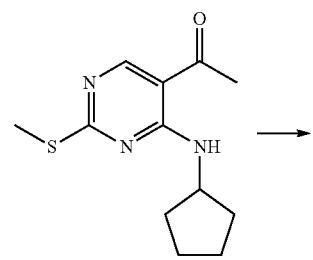

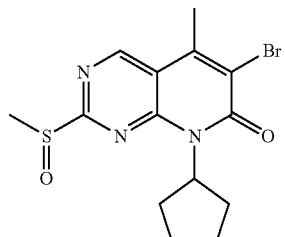

Intermediate A'

With regard to the existing process defects, developing an economical and environmentally friendly preparation technology with a simple process and superior quality, especially seeking a process technology which can adapt to industrial production, is of great realistic significance for improvement of economic and social benefits of this drug.

SUMMARY OF THE INVENTION

The purpose of this invention is to provide a method for preparing Palbociclib (I) which has readily available raw materials and a simple process, is economical and environmentally friendly, and is suitable for industrial production.

In order to realize the above purpose, the following main technical solution: a method for preparing Palbociclib (I) has been adopted in this invention,

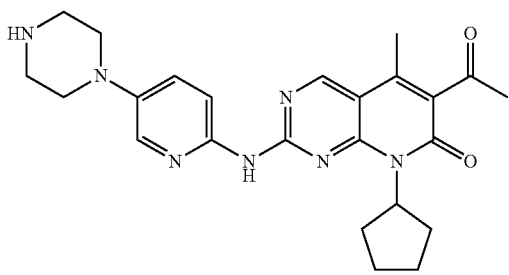

Palbociclib (I)

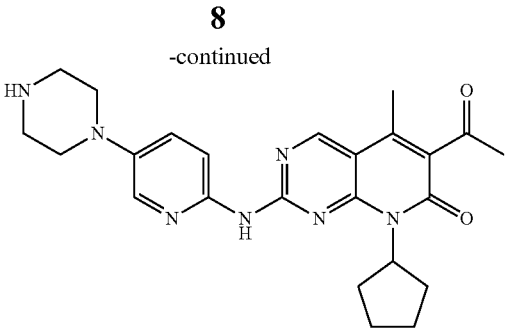

-continued

Palbociclib (I)

The method for preparing Palbociclib (I) comprises the steps of: produce the 6-acetyl-5-methyl-2-substituent-pyrido[2,3-d]pyrimidin-7(8H)-one (IV) through ring-closure reaction between the 1-(4-amino-2-substituent-5-pyrimidinyl)ethanone (II) and acetylacetic ester (III) ; produce the 6-acetyl-8-cyclopentyl-5-methyl-2-substituent-pyrido[2,3-d]pyrimidin-7(8H)-one (VI) through substitution reaction between the 6-acetyl-5-methyl-2-substituent-pyrido[2,3-d]pyrimidin-7(8H)-one (IV) and cyclopentane halide (V) in the existence of acid binding agents; produce the Palbociclib (I) through condensation and hydrolysis reactions between the 6-acetyl-8-cyclopentyl-5-methyl- 2-substituent-pyrido[2,3-d]pyrimidin-7(8H)-one (VI) and 4-(6-amino-3-pyridinyl)-1-piperazinecarboxylic acid 1,1-dimethylethyl ester (VII).

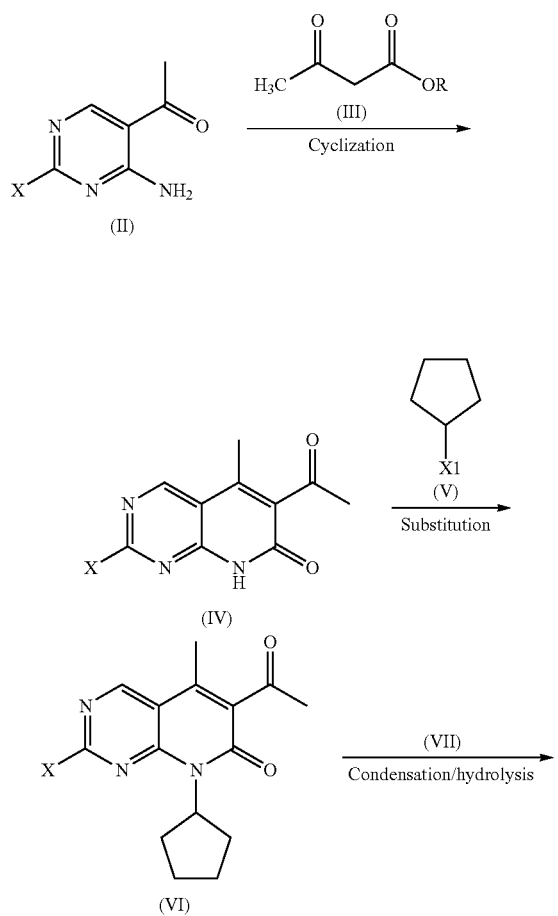

In addition, the following accessory technical solution has been proposed in this invention:

Substituent (X) in the mentioned 1-(4-amino-2-substituent-5-pyrimidinyl)ethanone (II) as raw materials is fluorine, chlorine, bromine, iodine, methylsulfinyl group or methylsulfonyl group, optimized chlorine or methylsulfinyl group.

The raw material of the mentioned acetylacetic ester (III) is methyl acetoacetate, ethyl acetoacetate, propyl acetoacetate, isopropyl acetoacetate, acetoacetic acid allyl ester or benzyl acetoacetate, optimized methyl acetoacetate or ethyl acetoacetate.

The molar ratio between the 1-(4-amino-2-substituent-5-pyrimidinyl)ethanone (II) and the acetylacetic ester (III) as raw materials of the mentioned ring-closure reaction is 1:1.0-2.0, with preference given to 1:1.0-1.5.

The halogens $X_1$ cyclopentane halide (V) as raw materials of the mentioned substitution reaction are fluorine, chlorine, bromine or iodine, with preference given to bromine or iodine.

The molar ratio between the 6-acetyl-5-methyl-2-substituent-pyrido[2,3-d]pyrimidin-7(8H)-one (IV) and cyclopentane halide(V) as raw materials of the substitution reaction is 1:1.0-2.0, with preference given to 1:1.1-1.3.

The acid binding agent of the mentioned substitution reaction is caesium carbonate, potassium carbonate, lithium carbonate, sodium tert-butoxide, potassium tert-butoxide or sodium hydride, with preference given to potassium tert-butoxide or sodium hydride.

The solvent for the mentioned substitution reaction of is dichloromethane, chloroform, 1,2-dichloroethane, acetonitrile, methylbenzene, tetrahydrofuran, dimethyl carbonate or dioxane, with preference given to dichloromethane or tetrahydrofuran.

The molar ratio to occur condensation between 6-acetyl-8-cyclopentyl-5-methyl-2-substituent-pyrido[2,3-d]pyrimidin-7(8H)-one (VI) and 4-(6-amino-3-pyridinyl)-1-piperazinecarboxylic acid 1,1-dimethylethyl ester (VII) as raw materials of the condensation reaction is 1:0.5-1.4, with preference given to 1:1.0-1.2.

The solvent of the mentioned condensation reaction is methylbenzene, xylene, N,N-dimethyl formamide, N,N-dimethylacetamide or dimethylsulfoxide, with preference given to methylbenzene or xylene.

The temperature of the mentioned condensation reaction is 50-150° C., with preference given to 50-80° C.

The mentioned hydrolysis reaction is acidic hydrolysis by using acids of hydrochloric acid, vitriol, phosphoric acid, acetic acid or trifluoroacetic acid, with preference given to hydrochloric acid.

Compared to the existing technology, the method for preparing Palbociclib (I) involved in this invention has the characteristics of having readily available raw materials and a simple process and being economical and environmentally friendly, so it is beneficial to industrial production of the API, thus promoting the development of economy and technology.

DETAILED DESCRIPTION OF THE PREFERRED EMBODIMENTS

The following nonrestrictive detailed description is hereby made towards the technical solutions in this invention in combination of several preferred embodiments. Hereinto, for the preparation of the raw material 4-(6-amino-3-pyridinyl)-1-piperazinecarboxylic acid 1,1-dimethylethyl ester (VII), refer to the method for preparing similar compounds in the reference *European Journal of Medicinal Chemistry* 81, 341-349; 2014.

Embodiment 1:

The 1-(4-amino-2-chlorine-5-pyrimidinyl)ethanone (II) (1.71 g, 10 mmol) and methyl acetoacetate (III) (1.28 g, 11 mmol) was added into the reaction tube and placed into the microwave oscillator of 700 watts after enclosure for about 8-10 minutes. They were cooled down to the room temperature. Reactants were dissolves with the dichloromethane and then washed with water, sodium bicarbonate solution of 10% and saturated salt solution, respectively; they were dried and concentrated with anhydrous sodium sulfates. The crude products obtained were recrystallized with normal hexane and ethyl acetate (1:1, V/V), and the off-white solid 6-acetyl-5-methyl-2-chlorine-pyrido[2,3-d]pyrimidin-7(8H)-one (IV) of 2.17 g was obtained through vacuum drying; yield: 91.6%; mass spectrum (EI): m/z 238 (M+H).

Embodiment 2:

The 1-(4-amino-2-methylsulfinyl-5-pyrimidinyl)ethanone (II) (2.0 g, 10 mmol) and ethyl acetoacetate (III) (1.43 g, 11 mmol) were added into the reaction tube and placed into the microwave oscillator of 700 watts after enclosure for about 9-12 minutes. Then, they were cooled down to the room temperature. Reactants were dissolved with the dichloromethane and washed with water, sodium bicarbonate solution of 10% and saturated salt solution, respectively; they were dried and concentrated with anhydrous sodium sulfates. The crude products obtained were recrystallized with normal hexane and ethyl acetate (1:2, V/V), the light yellow solids were obtained through vacuum drying by using 6-acetyl-5-methyl-2-methylsulfinyl-pyrido[2,3-d]pyrimidin-7(8H)-one (IV) of 2.25 g; yield: 84.9%; mass spectrometry (EI): m/z 266 (M+H).

Embodiment 3:

In the nitrogen atmosphere, the 6-acetyl-5-methyl-2-chlorine-pyrido[2,3-d]pyrimidin-7(8H)-one (IV) (1.2 g, 5 mmol), potassium tert-butoxide (0.84 g, 7.5 mmol) and N,N-dimethyl formamide of 15 mL were added into the reaction bulb. They were heated up to 65° C. and stirred to react for 30 minutes, and then cooled down to the room temperature. The cyclopentane bromide (1.1 g, 7.5 mmol) were added before they were heated up to 65° C. and stirred to react for 1 hour. The TLC detection reaction was completed. A quenching reaction was conducted with water, extraction was conducted with ethyl acetate for three times, and organic phases were combined. After drying and concentration with anhydrous sodium sulfate, solids were separated out. The crude products obtained were recrystallized with normal hexane and ethyl acetate (2:1, V/V), and 2.1 g of off-white solid 6-acetyl-8-cyclopentyl-5-methyl-2-chlorine-pyrido[2,3-d]pyrimidin-7(8H)-one (VI) of 1.1 g was obtained through vacuum drying; yield: 72.1%; mass spectrometry (EI): m/z 277 (M+H).

Embodiment 4:

In the nitrogen atmosphere, the 6-acetyl-5-methyl-2-methylsulfinyl-pyrido[2,3-d]pyrimidin-7(8H)-one (IV) (2.65 g, 10 mmol), silicone oil of 0.6 g containing 60% sodium hydride and the N,N-dimethyl formamide of 30 mL were added into the reaction bulb. They were heated up to 55° C. and stirred to react for 30 minutes, and then cooled down to the room temperature. The iodocyclopentane (2.94 g, 15 mmol) was added before they were heated up to 55° C. and stirred to react for 30 minutes. The TLC detection reaction was completed. A quenching reaction was conducted with water, extraction was conducted with ethyl acetate for three times, and organic phases were combined. After drying and concentration with anhydrous sodium sulfate, solids were separated out. The crude products obtained were recrystallized with normal hexane and ethyl acetate (2:1, V/V), and light yellow solids 6-acetyl-8-cyclopentyl-5-methyl-2-methylsulfinyl-pyrido[2,3-d]pyrimidin-7(8H)-one (VI) of 2.53 g were obtained through vacuum drying; yield: 76.3%; mass spectrometry (EI): m/z 334(M+H).

Embodiment 5:

In the nitrogen atmosphere, the 6-acetyl-8-cyclopentyl-5-methyl-2-chlorine-pyrido[2,3-d]pyrimidin-7(8H)-one (VI) (1.53 g, 5 mmol), 4-(6-amino-3-pyridinyl)-1- piperazinecarboxylic acid 1,1-dimethylethyl ester (VII) (2.78 g, 10 mmol), Lithium bis(trimethylsilyl)amide (2.0 g, 10 mmol) and methylbenzene of 50 mL were added into the reaction bulb. They were heated up to 50-55° C. and react for 2-3 hours, and then cooled down to the room temperature after the completion of TLC detection reaction. The organic layer was separated out by pouring the reaction mixture into icy water, extraction was conducted for the water layer with methylbenzene for two times, and organic phases were combined. The organic layer was washed with water and saline solution respectively, and dried and concentrated to dry with anhydrous sodium sulfate. The residues obtained were dissolved into the dichloromethane of 50 mL, which was added with the concentrated hydrochloric acid of 5 mL and stirred in the room temperature for 12 hours. The organic phase was separated out and washed with water and solution of 10% sodium bicarbonate. The solvent was recycled under normal pressure and added with diethyl ether to separate solids. The crude products obtained were recrystallized with normal hexane and ethyl acetate, and off-white solid Palbociclib (I) of 1.85 g was obtained; yield: 82.6%; mass spectrometry (EI): m/z 448(M+H).

Embodiment 6:

In the nitrogen atmosphere, the 6-acetyl-8-cyclopentyl-5-methyl-2-methylsulfinyl-pyrido[2,3-d]pyrimidin-7(8H)-one (VI) (1.67 g, 5 mmol), 4-(6-amino-3-pyridinyl)-1- piperazinecarboxylic acid 1,1-dimethylethyl ester (VII) (2.78 g, 10 mmol) and methylbenzene of 50 mL were added into the reaction bulb. They were heated up to 70-75° C. and react for 2-3 hours, and then cooled down to the room temperature after the completion of TLC detection reaction. The organic layer was separated out by pouring the reaction mixture into the icy water, extraction was conducted for the water layer with methylbenzene for two times, and organic phases were combined. The organic layer was washed with water and saline solution respectively, and dried and concentrated to dry with anhydrous sodium sulfate. The residues obtained were dissolved into the dichloromethane of 50 mL, which was added with the concentrated hydrochloric acid of 10 mL and stirred in the room temperature for 12 hours. The organic phase was separated out and washed with ammonium hydroxide of 5% and pure water. The solvent was recycled under normal pressure and added with diethyl ether to separate solids. The crude products obtained were recrystallized with normal hexane and ethyl acetate, and off-white solid Palbociclib (I) of 3.8 g was obtained; yield: 85.0%; mass spectrometry (EI): m/z 448(M+H).

Embodiment 7 [synthesis of 1-(4-amino-2-chlorine-5-pyrimidinyl)ethanone (II, X=Cl)]:

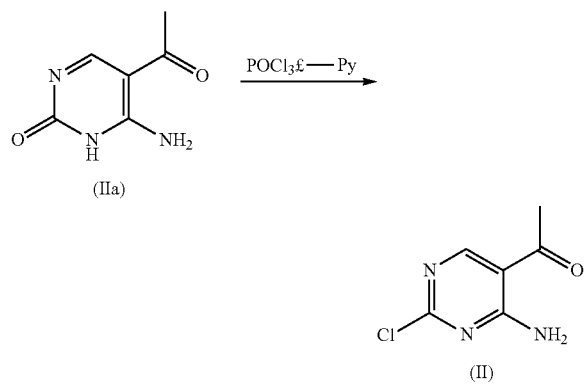

The 5-acetyl-6-amino-2(1H)-pyrimidinone (IIa, whose method for preparing shall refer to the preparation of similar compounds in the reference "Organic Preparations and Procedures International, 41 (6), 515-532; 2009") (4.6 g, 30 mmol), phosphorus oxychloride (6.8 g, 45 mmol) and methylbenzene of 25 mL were added into the reaction bulb. The pyridine (4.7 g, 60 mmol) was dropwise added into the ice-bath and the temperature was kept to no more than 25° C. After addition, the reaction mixture was heated up to 100-105 □ to react for 4 hours and the TLC detection reaction was completed. Then, the reaction mixture was cooled down to the room temperature and then poured slowly to the water of 100 mL to be stirred for 15 minutes. Extraction was conducted with methylbenzene for two times, and organic phases were combined. The reaction mixture was washed by using the saturated sodium bicarbonate, saturated salt solution and water and then dried with anhydrous sodium sulfate. After the vacuum distillation, the yellow oily substances 1-(4-amino-2-chlorine-5-pyrimidinyl)ethanone of (II) 4.5 g were obtained; yield: 87.0%.

Embodiment 8 [synthesis of 1-(4-amino-2-methylsulfinyl-5-pyrimidinyl)ethanone (II, X=methylsulfinyl group)]:

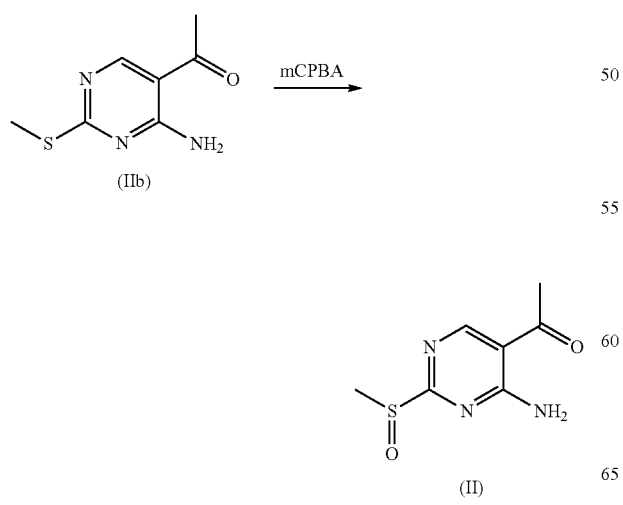

The 1-[4-amino-2-(methylthio)-5-pyrimidinyl]ethanone (IIb, whose method for preparing shall refer to the preparation of similar compounds in the reference "Journal of Medicinal Chemistry, 48(7), 2371-2387; 2005") (3.7 g, 20 mmol), metachloroperbenzoic acid (mCPBA) (5.2 g, 30 mmol) and dichloromethane (100 mL) were added into the reaction bulb to be stirred under room temperature and react for 12 hours, and the TLC detection reaction was completed. The reaction mixture was slowly poured into the saturated sodium bicarbonate solution of 50 mL and stirred for 15 minutes to stand for separation. Organic phases were dried with the anhydrous sodium sulfate. The extract was vacuum evaporated to recover the solvent. The crude products obtained were recrystallized with ethyl acetate, and white solid 1-(4-amino-2-methylsulfinyl-5-pyrimidinyl)ethanone (II) of 3.2 g was obtained; yield: 80.4%.

What needs to be pointed out is that the above embodiments are just to describe technical conceptions and characteristics of this invention, and their purpose is to enable the personnel knowing this technology well to understand contents of this invention and implement it accordingly, but protection scope of this invention cannot be restricted on this account. All equivalent changes or modifications made according to spiritual essence of this invention shall be covered in the protection scope of this invention.

What is claimed is:
1. A method for preparing palbociclib (I)

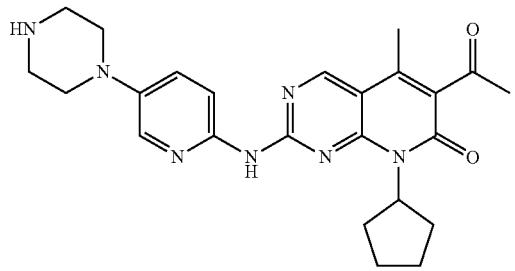

comprising:
producing 6-acetyl-5-methyl-2-X-pyrido[2,3-d]pyrimidin-7(8H)-one through a ring-closure reaction between 1-(4-amino-2-$X_1$-5-pyrimidinyl)ethanone and an acetoacetate;
producing 6-acetyl-8-cyclopentyl-5-methyl-2-X-pyrido[2,3-d]pyrimidin-7(8H)-one through a substitution reaction between 6-acetyl-5-methyl-2-X-pyrido[2,3-d]pyrimidin-7(8H)-one and a cyclopentane halide in the presence of an acid binding agent; and
preparing palbociclib (I) through a condensation reaction of 6-acetyl-8-cyclopentyl-5-methyl-2-X-pyrido[2,3-d]pyrimidin-7(8H)-one and 4-(6-amino-3-pyridinyl)-1-piperazinecarboxylic acid 1,1-dimethylethyl ester followed by a hydrolysis of the product of the condensation reaction; wherein:
X is chlorine, or methylsulfinyl;
$X_1$ is fluorine, chlorine, bromine, iodine, methylsulfinyl or methylsulfinyl; and
the acetoacetate is selected from the group consisting of methyl acetoacetate, ethyl acetoacetate, propyl acetoacetate, isopropyl acetoacetate, allyl acetoacetate, and benzyl acetoacetate.

2. The method according to claim 1, wherein:
a molar ratio between 1-(4-amino-2-$X_1$-5-pyrimidinyl)ethanone and the acetoacetate is from 1:1.0 to 1:2.0.

3. The method according to claim 1, wherein:

a molar ratio between 6-acetyl-5-methyl-2-X-pyrido[2,3-d]pyrimidin-7(8H)-one and the cyclopentane halide is from 1:1.0 to 1:2.0; and the halogen of the cyclopentane halide is fluorine, chlorine, bromine or iodine.

4. The method according to claim 1, wherein:

the acid binding agent for the substitution reaction is caesium carbonate, potassium carbonate, lithium carbonate, sodium tert-butoxide, potassium tert-butoxide, or sodium hydride.

5. The method according to to claim 1, wherein:

a solvent for the substitution reaction is dichloromethane, chloroform, 1,2-dichloroethane, acetonitrile, methylbenzene, tetrahydrofuran, dimethyl carbonate, or dioxane.

6. The method according to claim 1, wherein:

a molar ratio between 6-acetyl-8-cyclopentyl-5-methyl-2-X-pyrido[2,3-d]pyrimidin-7(8H)-one of the condensation reaction and 4-(6-amino-3-pyridinyl)-1-piperazinecarboxylic acid 1,1-dimethylethyl ester is from 1:0.5 to 1:1.4.

7. The method according to claim 1, wherein:

a solvent for the condensation reaction is methylbenzene, xylene, N,N-dimethyl formamide, N,N-dimethylacetamide, or dimethylsulfoxide.

8. The method according to claim 1, wherein:

a temperature of the condensation reaction is 50-150° C.

9. The method according to claim 1, wherein:

the hydrolysis reaction is an acidic hydrolysis using an acid selected from the group consisting of hydrochloric acid, vitriol, phosphoric acid, acetic acid, and trifluoroacetic acid.

* * * * *